(12) United States Patent
Smith et al.

(10) Patent No.: US 9,387,040 B2
(45) Date of Patent: Jul. 12, 2016

(54) MULTI-SPOT LASER SURGICAL PROBE USING FACETED OPTICAL ELEMENTS

(71) Applicant: ALCON RESEARCH, LTD., Fort Worth, TX (US)

(72) Inventors: Ronald T. Smith, Irvine, CA (US); Michael Arthur Zica, Costa Mesa, CA (US); Dustin Jacob Bouch, Petaluma, CA (US)

(73) Assignee: ALCON RESEARCH, LTD., For Worth, TX (US)

( * ) Notice: Subject to any disclaimer, the term of this patent is extended or adjusted under 35 U.S.C. 154(b) by 117 days.

(21) Appl. No.: 14/560,645

(22) Filed: Dec. 4, 2014

(65) Prior Publication Data

US 2015/0094699 A1     Apr. 2, 2015

Related U.S. Application Data

(62) Division of application No. 13/565,041, filed on Aug. 2, 2012, now abandoned.

(60) Provisional application No. 61/521,447, filed on Aug. 9, 2011.

(51) Int. Cl.
    *A61F 9/008*     (2006.01)
    *A61B 18/20*     (2006.01)
    (Continued)

(52) U.S. Cl.
    CPC .............. *A61B 18/20* (2013.01); *A61B 1/00066* (2013.01); *A61B 1/00096* (2013.01);
    (Continued)

(58) Field of Classification Search
    CPC .. A61F 9/00821; A61B 18/201; A61B 18/22; A61B 2018/2261; A61B 2018/2272; A61B 2018/2277; A61B 2018/2294; A61B 1/00096; A61B 1/0017; A61B 1/07; G02B 6/3845
    USPC ............... 362/572–575; 385/43, 78; 600/176, 600/182; 606/2–19; 607/88, 89
    See application file for complete search history.

(56) References Cited

U.S. PATENT DOCUMENTS

| | | | |
|---|---|---|---|
| 3,682,171 | A | 8/1972 | Dali et al. |
| 4,182,017 | A | 1/1980 | Ford et al. |

(Continued)

FOREIGN PATENT DOCUMENTS

| | | |
|---|---|---|
| CN | 101365404 A | 2/2009 |
| JP | 1992092655 A | 3/1992 |

(Continued)

OTHER PUBLICATIONS

International Search Report and Written Opinion, PCT/US2012/049297, International Searching Authority, Oct. 2012, 6 pgs.

*Primary Examiner* — Lynsey Crandall
*Assistant Examiner* — Nathan J Jenness
(74) *Attorney, Agent, or Firm* — Jason Finch

(57) ABSTRACT

An optical surgical probe includes a handpiece having a metal cannula at a distal end, a light guide within the metal cannula that carries a light beam from a light source through the metal cannula, and a multi-spot generator formed within a distal opening of the metal cannula that seals the distal opening of the metal cannula. The multi-spot generator includes a proximally-facing faceted end surface spaced from a distal end of the light guide that includes at least one facet oblique to a path of the light beam and a ball lens located distal to the faceted end surface. A high-conductivity ferrule surrounds the distal end of the light guide, is in thermal contact with the metal cannula, and includes a side-shield portion extending beyond the distal end of the light guide. The ferrule shields the cannula from a portion of the light beam reflected by the faceted end surface.

4 Claims, 1 Drawing Sheet

(51) Int. Cl.
  *A61B 1/00* (2006.01)
  *A61B 1/07* (2006.01)
  *A61B 1/12* (2006.01)
  *A61B 18/22* (2006.01)
  *A61B 18/00* (2006.01)

(52) U.S. Cl.
  CPC .............. *A61B 1/07* (2013.01); *A61B 1/128* (2013.01); *A61B 18/201* (2013.01); *A61F 9/00821* (2013.01); *A61B 2018/0091* (2013.01); *A61B 2018/2277* (2013.01); *A61F 2009/00863* (2013.01)

(56) References Cited

U.S. PATENT DOCUMENTS

| | | |
|---|---|---|
| 4,760,845 A | 8/1988 | Kovalcheck |
| 5,370,649 A | 12/1994 | Gardetto et al. |
| 5,507,742 A | 4/1996 | Long et al. |
| 5,588,949 A | 12/1996 | Taylor et al. |
| 6,053,862 A | 4/2000 | Ono |
| 6,270,492 B1 | 8/2001 | Sinofsky |
| 6,558,047 B1 | 5/2003 | Tran et al. |
| 7,235,073 B2 | 6/2007 | Levine et al. |
| 7,591,575 B2 | 9/2009 | Hama et al. |
| 7,783,346 B2 | 8/2010 | Smith et al. |
| 7,972,272 B2 | 7/2011 | Munce et al. |
| 2004/0184728 A1* | 9/2004 | Miao ................ G02B 6/32 385/33 |
| 2007/0027443 A1 | 2/2007 | Rose et al. |
| 2007/0255356 A1 | 11/2007 | Rose et al. |
| 2011/0141759 A1 | 6/2011 | Smith |
| 2011/0144627 A1 | 6/2011 | Smith |

FOREIGN PATENT DOCUMENTS

| | | |
|---|---|---|
| JP | 1994061338 B2 | 8/1994 |
| JP | 302589674 B | 3/1997 |
| JP | 09117407 A | 5/1997 |
| JP | 2001161708 A | 6/2001 |
| WO | 2007/133267 A1 | 11/2007 |

* cited by examiner

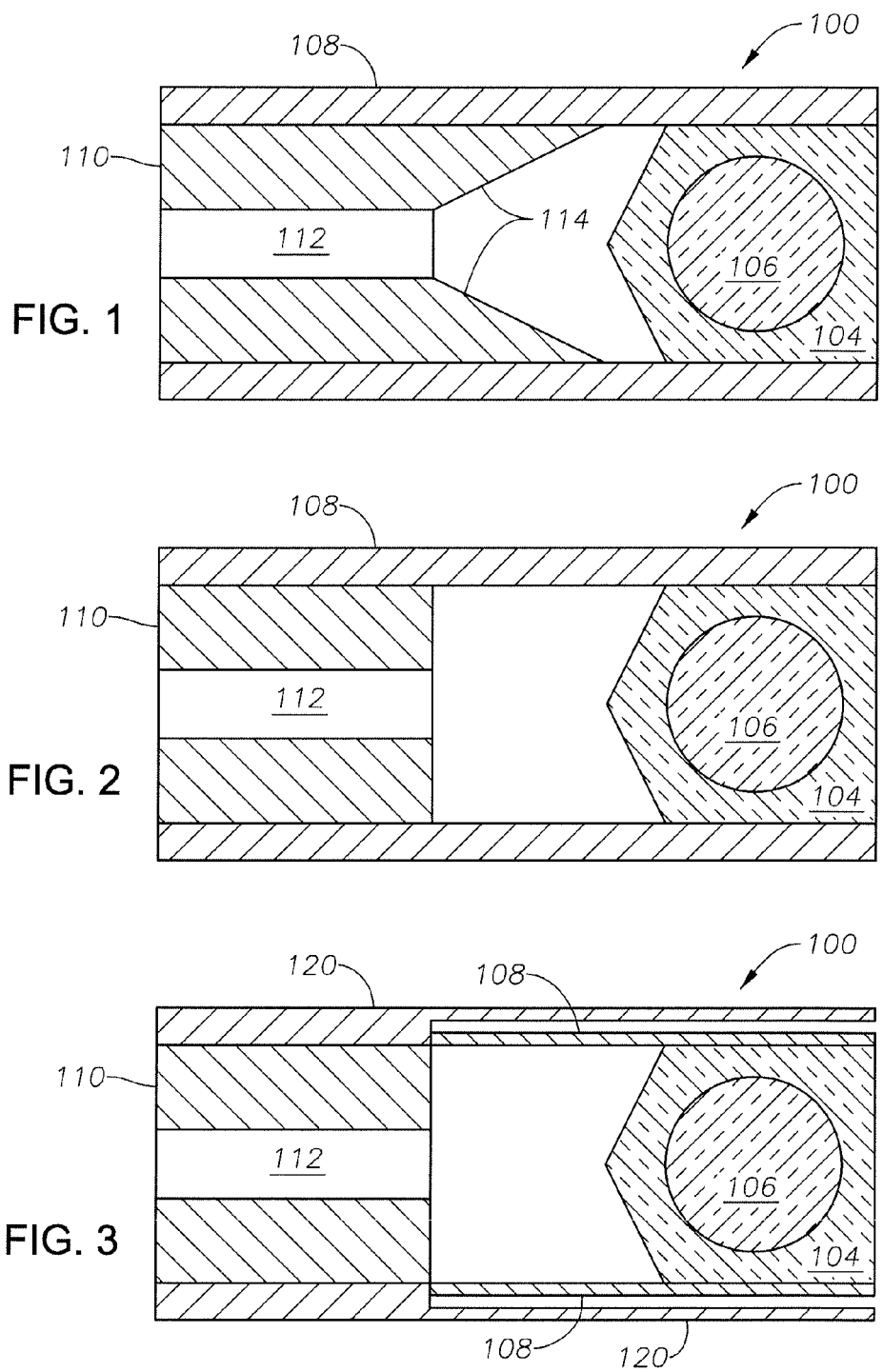

MULTI-SPOT LASER SURGICAL PROBE USING FACETED OPTICAL ELEMENTS

RELATED APPLICATIONS

This application is a divisional of U.S. application Ser. No. 13/565,041, filed Aug. 2, 2012, which claimed priority to U.S. provisional application Ser. No. 61/521,447, filed on Aug. 9, 2011, the contents of which are incorporated herein by reference. Additionally, this application is related to co-pending U.S. patent application Ser. No. 12/959,533, filed on Dec. 3, 2010, and commonly assigned with the present Application.

FIELD OF THE DISCLSORE

This invention relates to optical surgical probes and, more particularly, to a multi-spot laser surgical probe using faceted optical elements.

BACKGROUND

Optical surgical probes deliver light to a surgical field for a variety of applications. In some applications, it may be useful to deliver light to multiple spots in the surgical field. For example, in pan-retinal photocoagulation of retinal tissue, it may be desirable to deliver laser light to multiple spots so as to reduce the time of the pan-retinal photocoagulation procedure. Various techniques have been employed to produce multiple beams for a multi-spot pattern. For example, one approach uses a diffractive beam splitter element to divide an incoming beam into multiple spots that are coupled into multiple optical fibers that deliver the multiple spots to the retina. But it is also desirable to have a multi-spot generator that can be placed at a distal end of the optical surgical probe to more easily produce multiple spots from a single input beam, so that the multi-spot generator can more easily be used with existing laser sources without the need for additional components to align the laser surgical probe with the sources.

Difficulties can arise in the use of a diffractive beam splitter element at a distal end of the optical surgical probe. As one example, a diffractive beam splitter element produces a multitude of higher diffraction orders, and while these orders are relatively lower in light intensity as compared to the primary spot pattern, they may not always be negligible in terms of their effects. As another example, a diffractive element may not perform identically in different refractive media. For example, if the diffractive beam splitter element is placed into a medium other than air, such as saline solution or oil, the recessed portions of the microscopic surface relief structure of the diffractive beam splitter element can be filled with material having a different refractive index than air, which can ruin the spot pattern. As yet another example, the spacing between the spots can vary for different wavelengths, which can be problematic when an aiming beam is of a certain color while a treatment beam is of a different color. Lastly, diffractive elements are frequently expensive and difficult to produce, and this is particularly the case when the diffractive element must be constructed to fit into a small area, such as a distal tip of a surgical probe for surgical instruments that are 23-gauge or smaller. Thus, there remains a need for an optical surgical probe that can produce multiple spots at a target area using optical elements at a distal end of the surgical probe.

SUMMARY

Particular embodiments of the present invention provide a thermally robust optical surgical probe including a multi-spot generator with a faceted optical adhesive element. In particular embodiments, an optical surgical probe includes a handpiece having a metal cannula located at a distal end of the handpiece, a light guide extending within the metal cannula and configured to carry a light beam from a light source through the metal cannula, and a multi-spot generator formed within a distal opening of the metal cannula and configured to seal the distal opening of the metal cannula. The multi-spot generator includes a faceted end surface spaced from a distal end of the light guide facing proximally within the metal cannula and including at least one facet oblique to a path of the light beam and a ball lens located distal to the faceted end surface. A high-conductivity ferrule surrounds the distal end of the light guide and is in thermal contact with the metal cannula. The high-conductivity ferrule includes a side-shield portion extending beyond the distal end of the light and is configured to shield the cannula from a portion of the light beam reflected by the faceted end surface of the multi-spot generator.

Other objects, features and advantages of the present disclosure will become apparent with reference to the drawings, and the following description of the drawings and claims.

BRIEF DESCRIPTION OF THE DRAWINGS

FIG. 1 illustrates a multi-spot generator with a highly thermally conductive ferrule according to a particular embodiment of the present disclosure;

FIG. 2 illustrates a multi-spot generator with a transparent cannula according to a particular embodiment of the present disclosure; and FIG. 3 illustrates a multi-spot generator with a transparent cannula according to an alternative embodiment of the present disclosure.

DETAILED DESCRIPTION

Co-pending U.S. application Ser. No. 12/959,533, filed on Dec. 3, 2010 and commonly assigned with the present Application, describes a multi-spot optical surgical probe using faceted optical adhesive. Various embodiments of the present disclosure provide additional features to facilitate the use of faceted optical adhesive in optical surgical probes. In particular, certain embodiments of the present disclosure provide a thermally robust optical surgical probe using faceted optical adhesive. As described in detail below, particular embodiments of the present disclosure incorporate additional features to reduce the likelihood that "hot spots" will develop in the surgical probe that could cause the faceted optical adhesive or the adhesive joining the ferrule and the cannula to degrade and/or fail.

In certain embodiments of the present disclosure, a ferrule located within the distal end of the probe is modified to improve its ability to conduct heat away from the distal tip of the probe. The first modification is to change the material from the typically-used, low-thermal-conductivity stainless steel to a material with a much higher thermal conductivity such as copper or silver. The ferrule material need not necessarily be biocompatible since it is physically isolated from the outside of the probe. This permits the selection of a non-biocompatible material such as copper or silver that has much higher thermal conductivity than any available biocompatible materials. The higher thermal conductivity enables more efficient conduction of heat away from the distal end of the probe. The second modification is to add to the cylindrical ferrule a distal side-shield that prevents light reflected off of the adhesive facets from illuminating and being absorbed by the cannula. Instead, reflected light illuminates and is substantially absorbed by the high-thermal-conductivity ferrule that efficiently conducts the heat away from the distal end of the probe.

In an alternative embodiment of the present disclosure, the absorptive cannula is replaced with a transparent cannula that transmits reflected light from the adhesive facets into the ambient region outside of the cannula. This results in a significant reduction in the temperature of the distal end of the probe. Since high intensity transmitted light directed toward the surgeon may interfere with his view of the retina, various means are available to block or dissipate this light, including a reflective, diffusive or translucent layer on the outside of the transparent cannula and an opaque cylindrical cannula outside of the transparent cannula and physically separated from it by an insulating air gap. This opaque cannula need not necessarily be made from a highly thermally conductive material but it can be made from a stiff and strong material such as stainless steel which provides added structural strength to the distal end of the probe.

FIG. 1 illustrates a multi-spot generator 100 according to a particular embodiment of the present disclosure suitable for placement at a distal end of an optical surgical probe. In the depicted embodiment, a faceted optical adhesive 104 having a ball lens 106, such as a sapphire ball lens, is located within a cannula 108. Within the cannula 108 is a high-conductivity ferrule 110 holding an optical fiber 112. The optical fiber 112 delivers light, such as laser light, from an illumination source (not shown).

The high-thermal-conductivity ferrule 110 (hereinafter referred to as "high-conductivity ferrule") is formed from a material with a thermal conductivity significantly higher than the stainless steel material ordinarily used in optical surgical probes, which is typically around 15 W/m-K. For purposes of this specification, "high-conductivity" will refer to materials having thermal conductivity in excess of 100 W/m-K. Suitable examples include copper (conductivity of 372 W/m-K), sterling silver (410 W/m-K), or pure silver (427 W/m-K). Because the high-conductivity ferrule 110 is encapsulated within the cannula 108 by the faceted optical adhesive 104, the high-conductivity ferrule 110 need not be made of a biocompatible material, which allows consideration of high-conductivity materials that are not ordinarily used in optical surgical probes.

The high-conductivity ferrule 110 includes a side-shield 114 extending distally past the optical fiber 112. The side-shield 114 is oriented to receive light reflected from facets of the faceted optical adhesive 104. While reflections from the faceted optical adhesive 104 are relatively low in energy compared to the incident beam (approximately 5% of incident energy), such reflections can nonetheless produce "hot spots" on the cannula 108. Given that the cannula 108 is ordinarily formed from stainless steel or other relatively poorly conducting material that is also not highly reflective, this can result in laser energy being absorbed, which in turn creates the potential for excess heat to accumulate near the faceted optical adhesive 104 or near the adhesive that bonds the ferrule 110 to the cannula 114 (not shown). This can degrade the performance of the optical surgical probe. The side-shield 114 intercepts the reflected beams to prevent them from reaching the cannula, and because the material of the ferrule 110 is highly conductive, any heat produced by absorption of the reflected beams in the ferrule 110 is rapidly dispersed, preventing the equilibrium temperature of the ferrule 110 from being significantly raised.

FIG. 2 illustrates an alternative embodiment of a thermally robust multi-spot generator according to the present disclosure. In the depicted embodiment, cannula 108 is formed of a transparent material. The material is preferably biocompatible, but if it is not, the outer surface cannula 108 may also be coated or treated to improve biocompatibility. The transparent cannula 108 allows the reflected light to pass through the cannula 108 to avoid forming hot spots. In particular embodiments, the cannula 108 is diffusive, so that the escaping light does not form visible light spots that could be distracting for a surgeon. For example, the surface of the cannula 108 could be formed from a translucent material, could be chemically or mechanically frosted (such as by scraping or acid etching), or could be coated with a diffusive coating. In alternative embodiments, the cannula 108 is transparent, but surrounded with a reflective coating, such as silver. The reflective coating prevents light from escaping into the surgeon's field of view while still reflecting the light away from the faceted optical adhesive 104, allowing the heat to be conducted away from the tip easily. The outer surface of the silver or reflective coating can be oxidized or coated to improve biocompatibility.

FIG. 3 illustrates an alternative embodiment of the transparent cannula 108. In the depicted embodiment, an opaque outer cannula 120 surrounds the transparent cannula 108. The opaque outer cannula 120 may be formed from conventional biocompatible materials, and it is preferably relatively absorptive, although it need not be highly conductive. The outer cannula 120 and the transparent cannula 108 are separated by an air gap. The air gap provides thermal insulation between the transparent cannula 108, and the transparent cannula 108 may also be formed from an insulative material like glass. Whatever heat is produced in the outer cannula 120 may be conducted away into other parts of the probe or the biological material surrounding the outer cannula 120. The thermal insulation between the outer cannula 120 and the faceted optical adhesive 104 reduces the likelihood of excess heat from accumulating near the faceted optical adhesive 104.

The embodiments of the present disclosure illustrated herein are exemplary, and various modifications may be made by a person of ordinary skill in the art. It should be understood that various changes, substitutions and alterations can be made hereto without departing from the scope of the present disclosure.

What is claimed is:

1. An optical surgical probe comprising:
    a handpiece comprising a metal cannula, the metal cannula located at a distal end of the handpiece;
    a light guide extending within the metal cannula, the light guide configured to carry a light beam from a light source through the metal cannula;
    a multi-spot generator formed within a distal opening of the metal cannula and configured to seal the distal opening of the metal cannula, the multi-spot generator comprising:
        a faceted end surface spaced from a distal end of the light guide facing proximally within the metal cannula, the faceted end surface including at least one facet oblique to a path of the light beam; and
        a ball lens located distal to the faceted end surface; and
    a high-conductivity ferrule surrounding the distal end of the light guide and being in thermal contact with the metal cannula, the high-conductivity ferrule comprising a side-shield portion extending beyond the distal end of the light guide and configured to shield the cannula from a portion of the light beam reflected by the faceted end surface of the multi-spot generator.

2. The probe of claim 1, wherein the high-conductivity ferrule is formed of silver.

3. The probe of claim 1, wherein the high-conductivity ferrule is formed of copper.

4. The probe of claim 1, wherein the high-conductivity ferrule has a thermal conductivity of at least 372 W/m-K.

* * * * *